United States Patent
Musick

(10) Patent No.: US 9,115,286 B2
(45) Date of Patent: *Aug. 25, 2015

(54) TREATED INORGANIC PARTICLE

(75) Inventor: Charles David Musick, Waverly, TN (US)

(73) Assignee: THE CHEMOURS COMPANY TT, LLC, Harrisburg, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/125,668

(22) PCT Filed: Jun. 20, 2012

(86) PCT No.: PCT/US2012/043233
§ 371 (c)(1),
(2), (4) Date: Dec. 12, 2013

(87) PCT Pub. No.: WO2013/003137
PCT Pub. Date: Jan. 3, 2013

(65) Prior Publication Data
US 2014/0102333 A1    Apr. 17, 2014

Related U.S. Application Data

(60) Provisional application No. 61/501,800, filed on Jun. 28, 2011.

(51) Int. Cl.
*C09D 5/00* (2006.01)
*C09D 5/14* (2006.01)
*C09C 1/36* (2006.01)
*C09C 3/06* (2006.01)

(52) U.S. Cl.
CPC .............. *C09C 1/3661* (2013.01); *C09C 1/3653* (2013.01); *C09C 3/06* (2013.01); *C09C 3/063* (2013.01); *C01P 2004/62* (2013.01); *C01P 2004/82* (2013.01)

(58) Field of Classification Search
CPC .............. C09C 2200/1004; C09C 1/0009; C09C 1/3661; C09C 1/36; C09C 5/00; C09C 5/14; C09C 7/00
See application file for complete search history.

(56) References Cited

U.S. PATENT DOCUMENTS

| 3,528,837 | A | 9/1970 | Sheehan | |
|---|---|---|---|---|
| 3,640,743 | A | 2/1972 | Sheehan | |
| 5,180,585 | A | 1/1993 | Jacobson et al. | |
| 5,456,749 | A * | 10/1995 | Iwasa et al. | 106/417 |
| 5,503,840 | A * | 4/1996 | Jacobson et al. | 424/421 |
| 6,569,529 | B1 * | 5/2003 | Phillips et al. | 428/403 |
| 7,029,648 | B2 | 4/2006 | Subramanian et al. | |
| 2006/0204456 | A1 | 9/2006 | Asakura | |
| 2008/0110497 | A1 | 5/2008 | Inoue et al. | |
| 2011/0104220 | A1 * | 5/2011 | Schmidt et al. | 424/401 |

FOREIGN PATENT DOCUMENTS

| EP | 1674517 A1 | 6/2006 |
|---|---|---|
| GB | 1459025 | 12/1976 |
| GN | 2242679 A | 10/1991 |
| WO | 95/10940 A1 | 4/1995 |

OTHER PUBLICATIONS

European Search Report, TT0105PCT, International Application No. PCT/US2012/043233, Dated Sep. 12, 2012.
H. B. Clark, "Titanium Dioxide Pigments", Treatise on Coatings, vol. 3, Pigments, Marcel Dekker, 1975 (Book Not Included).

* cited by examiner

*Primary Examiner* — Pegah Parvini

(57) ABSTRACT

The disclosure provides a treated inorganic particle, in particular a titanium dioxide particle, having reduced photoactivity, lower acid solubility and improved anti-microbial properties comprising: an inorganic core particle, in particular a titanium dioxide particle; a first treatment of silica, wherein the silica is added in a single step; and a second treatment comprising co-precipitated zinc oxide and alumina. These particles have reduced photoactivity, lower acid solubility and improved anti-microbial properties.

17 Claims, No Drawings

TREATED INORGANIC PARTICLE

BACKGROUND OF THE DISCLOSURE

1. Field of the Disclosure

This disclosure relates to an inorganic particle, in particular an inorganic oxide pigment particle, and more particularly a titanium dioxide pigment, $TiO_2$, suitable for use in coatings, plastic and laminates.

2. Background of the Disclosure

Titanium dioxide pigments are prepared using either the chloride process or the sulfate process. In the preparation of titanium dioxide pigments by the vapor phase chloride process, titanium tetrachloride, $TiCl_4$, is reacted with an oxygen containing gas at temperatures ranging from about 900° C. to about 1600° C., the resulting hot gaseous suspension of $TiO_2$ particles and free chlorine is discharged from the reactor and must be quickly cooled below about 600° C., for example, by passing it through a conduit, i.e., a flue, where growth of the titanium dioxide pigment particles and agglomeration of said particles takes place.

It is known to add various substances, such as silicon compounds and aluminum compounds, to the reactants in order to improve the pigmentary properties of the final product. Silicon compounds added as a coating to the TiO2 particles are known to reduce photoactivity of the TiO2 particles and improve durability of paints produced from such pigments. Alumina compounds are known to improve the dispersability of the pigments produced.

A need exists for a process for the addition of silica, aluminum and zinc to inorganic oxide pigments, and in particular titanium dioxide pigments, that provides property improvements needed for making improved coatings, plastic and laminates.

SUMMARY OF THE DISCLOSURE

In a first aspect, this disclosure provides a treated inorganic particle, typically an inorganic pigment particle, and more typically a titanium dioxide particle, having reduced photoactivity and improved anti-microbial properties comprising:
  (a) a inorganic core particle, typically titanium dioxide;
  (b) a first treatment of a silicon compound, such as silica, wherein the silicon compound is added in a single step; and
  (c) a second treatment comprising co-precipitated zinc oxide and alumina.

In a second aspect, this disclosure provides a process for forming a treated inorganic particle, more typically a titanium dioxide particle having reduced photoactivity, lower acid solubility, and improved anti-microbial properties comprising:
  (a) forming an aqueous suspension of inorganic particles, typically inorganic pigment particles, and more typically titanium dioxide particles;
  (b) depositing a first treatment of a silicon compound, such as silica, on the inorganic particles, more typically titanium dioxide particles, wherein the silicon compound is added in a single step;
  (c) depositing a second treatment over the first treatment, said second treatment comprising co-precipitated zinc oxide and alumina; and
  (d) recovering the solids, washing free from water soluble species and drying. This process further comprises micronizing the dried particles.

By "co-precipitated" we mean the simultaneous or substantially simultaneous precipitation of zinc oxide and alumina.

DETAILED DESCRIPTION OF THE DISCLOSURE

In this disclosure "comprising" is to be interpreted as specifying the presence of the stated features, integers, steps, or components as referred to, but does not preclude the presence or addition of one or more features, integers, steps, or components, or groups thereof. Additionally, the term "comprising" is intended to include examples encompassed by the terms "consisting essentially of" and "consisting of." Similarly, the term "consisting essentially of" is intended to include examples encompassed by the term "consisting of."

In this disclosure, when an amount, concentration, or other value or parameter is given as either a range, typical range, or a list of upper typical values and lower typical values, this is to be understood as specifically disclosing all ranges formed from any pair of any upper range limit or typical value and any lower range limit or typical value, regardless of whether ranges are separately disclosed. Where a range of numerical values is recited herein, unless otherwise stated, the range is intended to include the endpoints thereof, and all integers and fractions within the range. It is not intended that the scope of the disclosure be limited to the specific values recited when defining a range.

In this disclosure, terms in the singular and the singular forms "a," "an," and "the," for example, include plural referents unless the content clearly dictates otherwise. Thus, for example, reference to "$TiO_2$ particle", "the $TiO_2$ particle", or "a $TiO_2$ particle" also includes a plurality of $TiO_2$ particles.

This disclosure relates to novel pigment compositions comprising inert inorganic particles, typically titanium dioxide particles, having a first treatment of a silicon compound such as silicon dioxide or silica, zinc silicates, or borosilicates, more typically silicon dioxide, and a second treatment of zinc oxide and aluminum oxide that may be used in paints, coatings, roofing materials, caulks, grouts, cements and masonry products and shaped polymeric articles including, but not limited to, films, membranes, fibers, and mono-filaments including but not limited to mono-filaments for brushes. In many applications, the compositions of this disclosure can be used to replace all or part of fillers and/or pigments normally used in the product. For example, if $TiO_2$, is selected as the core inorganic material, then the resulting particle, when incorporated into a fiber, will deluster the fiber and may also confer anti-microbial activity. The compositions of this disclosure are particularly useful when incorporated in a polymer carrier matrix composite. The physical properties of such composites are similar to those of the polymers themselves.

The inorganic core particles may be oxides of titanium, aluminum, zinc, copper, iron; the sulfates of calcium, strontium, barium; zinc sulfide; copper sulfide, zeolites; mica; talc; kaolin, mullite, calcium carbonate, or silica. Lead or mercury compound are contemplated equivalent core materials but may be undesirable due to their toxicity. More typical core materials are titanium dioxide, $TiO_7$ and barium sulfate, and most typically titanium dioxide, $TiO_7$.

In a specific embodiment, the $TiO_2$ can be prepared by any of several well-known methods including high temperature vapor phase oxidation of titanium tetrachloride, vapor phase hydrolysis of titanium tetrachloride, hydrolysis of colloidally seeded sulfuric acid solutions of titaniferous raw materials such as ilmenite, and the like. Such processes are well-known in the prior art.

Because the pigment of this disclosure is to be used in applications requiring high gloss, the size of the initial titanium dioxide core particles should typically be less than one micron, with the average typically falling between 0.15 and 0.25 micron.

Treatments to be applied by the process of this disclosure to the core particles of titanium dioxide can be applied by precipitation in aqueous slurries of the core titanium dioxide particles.

The treatments applied to the core particles in accordance with this disclosure are either porous or dense. The first treatment is with a silicon compound that may be silica or silicon dioxide, zinc silicate, or borosilicate. Silica is typically used because of the ease with which dense, uniform coatings may be obtained. It is applied from a solution of sodium silicate using techniques known to one skilled in the art. To obtain a dense silica treatment, a temperature above 50 C is typical and more typically above 70 C. The treatment corresponds to about 0.5 to about 20% by weight, more typically about 1 to about 7%, based on the total weight of the titanium dioxide core particle. Silica-coated particles may have a low isoelectric point and may tend to be difficult to disperse in organic materials. The isoelectric point represents the pH at which a particle surface carries zero electric charge. Control of the isoelectric point between 5.5 and 9.5 can be beneficial in facilitating the dispersion and/or flocculation of the particulate compositions during plant processing and in their end use applications.

The amount of silica added in a wet treatment process will often affect the acid solubility of the pigment produced by encapsulating the TiO2 particles. A well encapsulated $TiO_2$ particle will not be dissolved by a strong acid in the acid solubility test. A higher silica level will typically produce a $TiO_2$ product lower in acid solubility. While helpful for reducing acid solubility, the additional silica will typically have negative impacts on gloss, particle size and cost. It is known to add materials to the silica precipitation to improve the uniformity of the coverage of the silica on the $TiO_2$ particle. Borosilicate and zinc silicate are two examples of modifying the silica treatment to improve uniformity of the coverage.

An alternate method of adding a silica coating to the $TiO_2$ particle is a pyrogenic deposition disclosed in U.S. Pat. No. 7,029,648 which is incorporated herein by reference.

The second treatment comprises co-precipitated zinc oxide and aluminum oxide. These treatments are typically porous, applied from a solution of soluble aluminate and a zinc salt using techniques known to one skilled in the art. The pH of the solution during the aluminate treatment will typically range from 3 to 10 at a temperature from 10 C to 90 C. The treatment corresponds to about 0.5 to about 20% by weight, more typically about 1 to about 5%, based on the total weight of the titanium dioxide core particle. Less than about 0.5% can cause poor dispersibility of the pigment in paint formulations and an amount of porous treatment greater than about 20% can cause gloss degradation.

The porous treatment consists essentially of alumina and is obtained by precipitating a soluble aluminate in the presence of the core particles. By "soluble aluminate" is meant alkali metal salts of aluminate anions, for example, sodium or potassium aluminate. The soluble aluminates are generally dissolved at a pH of greater than 10 and are precipitated at a pH of less than 10 and preferably 7.5 to 9.5. Because substantially all of the alumina that is precipitated finds its way to a treatment on the core particles, it typically is only necessary to provide that amount of soluble aluminate to the slurry liquid which will result, after precipitation, in the appropriate degree of treatment.

The alumina may also be a dense treatment. The alumina for the dense treatment is obtained from a cationic source of alumina. The term "cationic source of alumina" refers to aluminum compounds that dissolve in water to yield an acidic solution. Examples include aluminum sulfate, aluminum chloride, aluminum fluoride, basic aluminum chloride, and the like.

The second treatment also comprises a co-precipitation of zinc oxide during the alumina treatment step. This treatment is a porous treatment and is applied from a solution of a zinc salt at a temperature of 10 C to 90 C, and more typically at 25 C to 80 C. The zinc oxide treatment is typically applied with the alumina treatment from a mixture of zinc chloride or zinc sulfate. The zinc oxide treatment is present in the amount of about 0.3% to about 5% by weight, more typically about 0.5% to about 3%, based on the total weight of the titanium dioxide core particle. An amount of porous treatment greater than about 3% ZnO can cause gloss degradation in a paint formulation; however, the loss of gloss will not hurt a product designed for the laminate industry.

The process for forming a treated inorganic particle, more typically a titanium dioxide particle, having reduced photoactivity, reduced acid solubility and improved anti-microbial properties comprises:
 (a) forming an aqueous suspension of inorganic particles, more typically titanium dioxide particles;
 (b) depositing a first treatment of silicon compound, such as silica, on the core inorganic oxide particles, more typically titanium dioxide particles, wherein the silicon compound is added in a single step;
 (c) depositing a second treatment over the first treatment, said second treatment comprising co-precipitated zinc oxide and alumina; and
 (d) recovering the solids, washing free from water soluble species and drying. This process further comprises micronizing the dried particles.

Typically, the silicon addition in step (b) occurs as a wet precipitation at a pH between 4 and 10, more typically between 7 and 9.5, and at a temperature between 50 C and 100 C, and more typically between 70 C and 90 C. Alternately, the silica is deposited pyrogenically as part of the vapor phase oxidation of $TiCl_4$.

Typically, the zinc and aluminate co-precipitation in step (c) occurs at a temperature between 10 C and 90 C, and more typically between 30 C and 80 C, and most typically between 50 C and 75 C.

After the treatments in accordance with this disclosure, the pigment is recovered by known procedures including filtration, washing, drying, sieving, and dry grinding such as micronizing.

The treated pigments of this disclosure are useful in coating and polymer applications and paper slurries. These may also be of particular value in cool roofing applications where both higher durability and higher L* from reduced mildew growth are desired.

Tests

In the examples which follow, the test results were obtained by the procedures described below.

Chalk Fade Durability

Durability of a pigment is usually measured as resistance to chalking in long-term (for example, 2 years) outdoor exposure tests of paints containing the pigment. Chalk/fade degradation of exterior paints containing $TiO_2$ pigments is partly attributed to catalytic action of the $TiO_2$ surface in oxidation of the organic binder in the presence of ultraviolet radiation, oxygen, and water vapor (H. B. Clark, "Titanium Dioxide Pigments", Treatise on Coatings, Vol. 3, Pigments, Marcel Dekker, 1975). In the following examples, the ultraviolet reactivity of $TiO_2$ pigments was measured by the above method. Typically semi-durable chalk fade durability is greater than about 20, a durable chalk fade durability is greater than about 30, and a super-durable pigment has a chalk fade durability of greater than 35, and more super-durable pigment has a chalk fade durability of greater than 45.

Alkyd Gloss

The comparative effect of a $TiO_2$ pigment on gloss of a paint layer was determined by preparing paints with the dry pigment of this disclosure and with pigment standards. Pigment samples were dispersed in an alkyd vehicle and the dispersion was sand-milled and reduced with resins to spray consistency. Aluminum panels were spray painted using automatic spraying equipment under controlled conditions to produce uniform film thickness and surface characteristics. The paint films were then baked. Finally, gloss was determined by measuring 20 degree reflectance of the panels with a Hunterlab D-48-7 glossmeter and calculating gloss in relation to reflectance values of the standards.

Emulsion Gloss

Emulsion (TFW-182) Gloss was determined by preparing an emulsion paint formulation using a slurry sample produced from 76.5% $TiO_2$ solids in water. 100 grams of emulsion gloss masterbatch based on acrylic emulsion resin (Primal AC-388 from Rohm & Haas, a subsidiary of Dow Chemicals, Midland, Mich.) (27% Pigment Volume Concentration) should be used. The paint was produced by mixing 100 grams of masterbatch, 40.3 grams of slurry, and 0.7 grams of water. Draw-downs of the paint were made on black PVC panels, the panels were dried for 3 hours in a constant temperature, constant humidity (CTCH) cabinet, and 60 degree gloss was measured using a Hunter gloss meter (available from Hunter Laboratories, Reston, Va.), and gloss was calculated in relation to reflectance values of standards.

Acid Solubility

Add solubility is determined as the amount of pigment that dissolves in hot concentrated sulfuric acid.

A small sample of pigment was placed in hot sulfuric acid (about 176° C.) and digested for an hour. The sample was then diluted with a measured amount of water and all particulate material was filtered out. A measured sample of the filtrate was then placed in a volumetric flask. Hydrogen peroxide was added to the flask to ensure all the titanium ions were in the proper oxidation state for their concentration to be determined spectrophotometrically at 400 nm. The flask was then filled to volume with 10% sulfuric acid. The absorbance was measured vs. a blank containing the same amount of hydrogen peroxide as was added to the sample in 10% sulfuric acid. The percent of titanium dioxide was read from a calibration curve prepared from known standards. Typically, a semi-durable pigment particle has an acid solubility of less than about 15, a durable pigment has an acid sol less than 9, and a super-durable pigment has an acid sol less than 6.

72 Hour Laminate Light Stability

72 Hour Laminate Light Stability is determined by measuring the color change in a melamine containing paper laminate coupon when exposed to UV light.

A small sample of $TiO_2$ (6.0 grams) is mixed with 60 grams of a 50% water/50% BLTM-817 (or BLTM 806) Melamine Formaldehyde Resin, manufacturer: BTL of Ohio, Toledo, Ohio, and the mixture is mixed in an Osterizer at high speed for a total of 2 minutes. A 1½"×7" filter paper strip is placed in the solution to become completely saturated. Excess solution is removed by drawing both sides of the paper strip across a glass rod. The impregnated paper strips are allowed to dry for 10 to 20 minutes and then placed in a 110 C oven for 15 minutes. The impregnated strips are then constructed into a laminated containing the following layers for fabrication: 1) Blotter, 2) Caul Plate 3) Overlay, 4) Top impregnated filter strip, 5) Bottom impregnated filter strip, 6) White sheet, 7) 3 sheets Kraft core stock, 8) White Sheet, 9) Overlay, 10) Caul plate, 11) Blotter. The constructed laminate is place in the preheated Carver press for 6 minutes at 300 F under 1000 psi of pressure. The color of this strip is measured via a Hunter Labscan for L*a*b*. The test strips are place in a weathering machine with UV irradiance intensity set at 1.1 W/m2 at 420 nm. The Black panel temperature is set to 63 C. The strip is exposed for 72 hours. Within 15 minutes of completing exposure, the L*a*b* is measured again. The 72 hour laminate light stability is measured as delta E*, Delta E* is calculated as follows:

$$\text{Delta } E^* = \text{Square Root}((\text{Delta } L^*)^2 + (\text{Delta } a^*)^2 + (\text{Delta } b^*)^2)$$

Typically, the pigment particle has a light stability of less than about 8, more typically less than about 6, and for a lightfast laminate a typical light stability is less than about 2.4.

Nujol Yellowing Test

This test determined resistance to yellowing in plastics, a measure of photochemical discoloration.

A masterbatch of test medium was made by compounding 100 grams of Nujol, 2 grams of butylated hydroxyl toluene (BHT), 2 grams of Tinuvin 770, a commercial hindered amine antioxidant, and 10 grams of Vaseline for thickening. 1.2 grams of masterbatch was mulled with 0.64 grams of the $TiO_2$ pigment to a smooth dispersion.

A doctor place was used to form a thin film of the masterbatch/pigment composite on a microscope slide. The color components L*, A*, and B*, were measured using a LabScan spectro-colorimeter. The film was exposed to 24 hours of ultra violet radiation in a temperature-controlled enclosed box. The color components were then measured. The change in b* is a measure of yellowing stability. The lower the value of delta b*, the pigment is more photo-stable. Commercially available photo-stable pigments for plastic's applications have a Nujol Yellowing value less than about 3.

EXAMPLES

The disclosure will be better understood with reference to the following illustrative examples. Properties of the pigments prepared as in the examples, and those of several commercial pigments, for comparison, are shown in the Tables. All percentages are on a weight basis.

Comparative Example 1

Five gallons of $TiO_2$ slurry at ~325 grams per liter concentration were added to a small stirred tank. The pH was adjusted to 9.5 using 20% caustic. The slurry was heated to 90 C. Sodium silicate solution was added to the small stirred tank over a period of 30 minutes in an amount sufficient to add 5.6% $SiO_2$. The pH was maintained at 9.5 with dilute hydrochloric acid. The material was stirred for 30 minutes. The slurry was cooled to 75 C with time and ice. The pH was lowered to 8.2 using hydrochloric acid. Sodium aluminate solution was added to the small stirred tank over a period of 60 minutes in an amount sufficient to add 1.2% Al2O3, The pH was held at 8.2 with dilute HCl. The material was stirred for 30 minutes. The material was filtered, dried, screened and micronized. Acid solubility, and 72-hour laminate light stability was measured on the pigment. The pigment was made into paint and emulsion gloss (TFW-182) was tested as described above.

Comparative Example 2

Five gallons of $TiO_2$ slurry at ~325 grams per liter concentration were added to a small stirred tank. The pH was adjusted to 9.5 using 20% caustic. The slurry was heated to 90 C. Sodium silicate solution was added to the small stirred tank over a period of 30 minutes in an amount sufficient to add 5.6% $SiO_2$ while zinc chloride was simultaneously added at an amount sufficient to add 0.3% ZnO to form a zinc silicate glass. The pH was maintained at 9.5 with dilute hydrochloric acid. The material was stirred for 30 minutes. The slurry was cooled to 75 C with time and ice. The pH was lowered to 8.2 using hydrochloric acid. Sodium aluminate solution was added to the small stirred tank over a period of 60 minutes in an amount sufficient to add 1.2% $Al_2O_3$. The pH was held at 8.2 with dilute HCl. The material was stirred for 30 minutes. The material was filtered, dried, screened and micronized. Acid solubility, and 72-hour laminate light stability was measured on the pigment. The pigment was made into paint and emulsion gloss (TFW-182) was tested as described above.

Example 1

Five gallons of $TiO_2$ slurry at ~325 grams per liter concentration were added to a small stirred tank. The pH was adjusted to 9.5 using 20% caustic. The slurry was heated to 90 C. Sodium silicate solution was added to the small stirred tank over a period of 30 minutes in an amount sufficient to add 5.6% $SiO_2$. The pH was maintained at 9.5 with dilute hydrochloric acid. The material was stirred for 30 minutes. The slurry was cooled to 75 C with time and ice. The pH was lowered to 8.2 using hydrochloric acid. Sodium aluminate solution was added to the small stirred tank over a period of 60 minutes in an amount sufficient to add 1.2% $Al_2O_3$. Simultaneously, a zinc chloride solution was added at an amount sufficient to add 0.3% ZnO. The pH was held at 8.2 with dilute HCl. The material was stirred for 30 minutes. The material was filtered, dried, screened and micronized. Acid solubility was measured on the pigment. The pigment was made into paint and emulsion gloss (TFW-182) was tested as described above. Results are shown in Table 1.

Example 2

Example 1 was repeated with the following exception: zinc chloride solution was added at an amount sufficient to add 0.5% ZnO. Results are shown in Table 1.

Example 3

Example 1 was repeated with the following exception: zinc chloride solution was added at an amount sufficient to add 1.0% ZnO. Results are shown in Table 1.

Example 4

Example 1 was repeated with the following exception: zinc chloride solution was added at an amount sufficient to add 1.5% ZnO. Results are shown in Table 1.

Results for Comparative Examples 1-2 and Examples 1-4

The paints produced in the six examples above were painted onto boards and given external North facing exposure to enhance mildew growth. Digital images of the boards were taken after 18 months of exposure and analyzed for discoloration using a Hunter Labscan to measure whiteness (L*) as a proxy for discoloration due to mildew growth (decreased L* with time equates to increased mildew growth). The data showed that the L* of the samples produced in the two comparative examples was statistically lower than the L* of the four samples with zinc co-precipitated with the alumina. The 18 Month L* data is shown in Table 1.

Acid solubility, and chalk fade durability were also measured on the pigments produced in the above examples. The results for these are below:

TABLE 1

| Example | Acid Solubility | Chalk Fade | Gloss | 18 month L* |
|---------|-----------------|------------|-------|-------------|
| C1 | 5.4 | 39 | 19.3 | 73.2 |
| C2 | 4.3 | 44 | 18.1 | 71.9 |
| 1 | 4.1 | 40 | 18.9 | 73.7 |
| 2 | 3.6 | 47 | 18.4 | 74.7 |
| 3 | 3.2 | 45 | 20.6 | 72.9 |
| 4 | 3.1 | 45 | 20.1 | 77.4 |

Comparative Example 3

Comparative Example 1 was repeated with the following exceptions: Sodium silicate solution was added in an amount sufficient to add 3% $SiO_2$. Sodium aluminate solution was added in an amount sufficient to add 1.3% $Al_2O_3$. Results are shown in Table 2.

Example 5

Comparative Example 3 was repeated with the following exception: Simultaneously with the addition of the sodium aluminate solution, a zinc chloride solution was added at an amount sufficient to add 1.6% ZnO. Results are shown in Table 2.

Example 6

Example 5 was repeated with the following exception: zinc chloride solution was added at an amount sufficient to add 2.3% ZnO. Results are shown in Table 2.

Example 7

Example 5 was repeated with the following exception: zinc chloride solution was added at an amount sufficient to add 3.6% ZnO. Results are shown in Table 2.

Results for Comparative Example 3 and Examples 5-7

The paints produced in the examples above were painted onto boards and given external North facing exposure to enhance mildew growth. Digital images of the boards were taken after 18 months of exposure and analyzed for discoloration using a Hunter Labscan to measure whiteness (L*) as a proxy for discoloration due to mildew growth. The data showed that the L* of the samples produced in the comparative example was statistically lower than the L* of the three sample with zinc co-precipitated with the alumina. The 18 month L* data is shown in Table 2.

TABLE 2

72-Hour Laminate

| Example | Acid Solubility | Light Stability (ΔE*) | Chalk Fade | Gloss | 18 Mo L* |
|---|---|---|---|---|---|
| C3 | 5.8 | 3.61 | 24 | 27.0 | 71.9 |
| 5 | 3.2 | 2.46 | 35 | 27.7 | 75.5 |
| 6 | 2.8 | 2.24 | 47 | 25.4 | 76.9 |
| 7 | 2.6 | 1.76 | 43 | 19.8 | 74.2 |

Comparative Example 4

5000 grams of $TiO_2$ containing 2% pyrogenically added $SiO_2$ was mixed with 15 liters of water and added to a small stirred tank. The pH was adjusted to 8.2 using 20% caustic. The slurry was heated to 75 C. Sodium aluminate solution was added to the small stirred tank over a period of 60 minutes in an amount sufficient to add 1.3% $Al_2O_3$. The pH was held at 8.2 with dilute HCl. The material was stirred for 30 minutes. The material was filtered, dried, and screened. Acid solubility was measured on the pigment. Results are shown in Table 3.

Example 8

Comparative Example 4 was repeated with the following exception: simultaneously with the sodium aluminate addition, a zinc chloride solution was added at an amount sufficient to add 1.0% ZnO. Results are shown in Table 3

TABLE 3

| Example | Acid Solubility |
|---|---|
| C4 | 12.7 |
| 8 | 10.3 |

Comparative Example 5

Five gallons of $TiO_2$ slurry at ~325 grams per liter concentration were added to a small stirred tank. The pH was adjusted to 9.5 using 20% caustic. The slurry was heated to 90 C. Sodium silicate solution was added to the small stirred tank over a period of 30 minutes in an amount sufficient to add 4.3% $SiO_2$. The pH was maintained at 9.5 with dilute hydrochloric acid. The material was stirred for 30 minutes. The slurry was cooled to 75 C with time and ice. The pH was lowered to 8.2 using hydrochloric acid. Sodium aluminate solution was added to the small stirred tank over a period of 60 minutes in an amount sufficient to add 1.2% Al2O3. The pH was held at 8.2 with dilute HCl. The material was stirred for 30 minutes. The material was filtered, dried, screened and micronized. Nujol Yellowing was measured on the pigment. The results are shown in Table 4.

Example 9

The procedure described in Comparative Example 5 was repeated with the following exception: simultaneously with the addition of sodium aluminate, a zinc chloride solution was added at an amount sufficient to add 1.5% ZnO.

Example 10

Example 9 was repeated with the following exception: zinc chloride solution was added at an amount sufficient to add 2.1% ZnO. Results are shown in Table 4.

Example 11

Example 9 was repeated with the following exception: zinc chloride solution was added at an amount sufficient to add 3.6% ZnO. Results are shown in Table 4.

TABLE 4

| Example | % ZnO | Nujol Yellowing |
|---|---|---|
| C5 | 0 | 3.8 |
| 9 | 1.5 | 1.3 |
| 10 | 2.1 | 1.0 |
| 11 | 3.6 | 0.9 |

What is claimed is:

1. A treated inorganic particle having reduced photoactivity and improved anti-microbial properties comprising:
   (a) an inorganic core particle;
   (b) a first treatment of silicon compound, wherein the silicon compound is added in a single step; and
   (c) a second treatment comprising co-precipitated zinc oxide and alumina.

2. The treated inorganic particle of claim 1 wherein the inorganic core particle is titanium dioxide.

3. The treated inorganic particle of claim 2 wherein the silicon compound is silica, zinc silicate or borosilicate.

4. The treated inorganic particle of claim 3 wherein the silicon compound is silica.

5. The treated inorganic particle of claim 4 wherein the silica is pyrogenically added silica.

6. The treated inorganic particle of claim 1 wherein the silicon compound is present in the amount of about 0.5 to about 20% by weight, based on the total weight of the inorganic core particle.

7. The treated inorganic particle of claim 6 wherein the silicon compound is present in the amount of about 1 to about 7% by weight, based on the total weight of the inorganic core particle.

8. The treated inorganic particle of claim 1 wherein the alumina is present in the amount of about 0.05% to 20% by weight calculated as Al2O3 and based on the total weight of the inorganic core particle.

9. The treated inorganic particle of claim 8 wherein the alumina is present in the amount of about 1% to about 5% by weight calculated as $Al_2O_3$ and based on the total weight of the inorganic core particle.

10. The treated inorganic particle of claim 1 wherein the zinc oxide is present in the amount of about 0.3 to about 5% by weight, based on the total weight of the inorganic core particle.

11. The treated inorganic particle of claim 10 wherein the zinc oxide is present in the amount of about 0.5 to about 3% by weight, based on the total weight of the inorganic core particle.

12. The treated inorganic particle of claim 2 having an acid solubility of less than about 15.

13. The treated inorganic particle of claim 12 having an acid solubility of less than about 6.

14. The treated inorganic particle of claim 2 having light stability of less than about 6.

15. The treated inorganic particle of claim 2 having chalk fade of greater than about 20.

16. The treated inorganic particle of claim 15 having chalk fade of greater than about 45.

17. The treated inorganic particle of claim 2 having Nujol yellowing less than 3.

\* \* \* \* \*